(12) United States Patent
Otsubo

(10) Patent No.: US 8,834,440 B2
(45) Date of Patent: Sep. 16, 2014

(54) PANTS TYPE DISPOSABLE DIAPER

(75) Inventor: Toshifumi Otsubo, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 399 days.

(21) Appl. No.: 12/863,018

(22) PCT Filed: Dec. 16, 2008

(86) PCT No.: PCT/JP2008/072819
§ 371 (c)(1),
(2), (4) Date: Nov. 23, 2010

(87) PCT Pub. No.: WO2009/090819
PCT Pub. Date: Jul. 23, 2009

(65) Prior Publication Data
US 2011/0060306 A1    Mar. 10, 2011

(30) Foreign Application Priority Data

Jan. 16, 2008  (JP) .................................. 2008-006555

(51) Int. Cl.
*A61F 13/495*  (2006.01)

(52) U.S. Cl.
CPC ....... *A61F 13/495* (2013.01); *A61F 2013/4953* (2013.01); *A61F 2013/4951* (2013.01)
USPC ................................ 604/385.19; 604/385.01

(58) Field of Classification Search
CPC ........... A61F 13/495; A61F 2013/4951; A61F 2013/4953
USPC ........ 604/385.19, 385.101, 400, 402, 385.08, 604/385.01, 378
See application file for complete search history.

(56) References Cited

U.S. PATENT DOCUMENTS 2,093,371 A  *  9/1937  Sheehy .............................. 2/407
4,397,645 A  *  8/1983  Buell ............................ 604/380
(Continued)

FOREIGN PATENT DOCUMENTS

GB        2268073       1/1994
JP        05305109      11/1993
(Continued)

OTHER PUBLICATIONS

International Search Report for PCT/JP2008/072819 issued Jan. 27, 2009.

*Primary Examiner* — Lynne Anderson
*Assistant Examiner* — Peter S Vasat
(74) *Attorney, Agent, or Firm* — Lowe Hauptman & Ham LLP

(57) ABSTRACT

The present invention aims to provide a pants type disposable diaper free from noticeable gathers formed on the innermost side of the crotch region. In the crotch region of the pants type disposable diaper, the bodily fluid-absorbent core is sandwiched between the liquid-permeable inner sheet and the liquid-impermeable outer sheet. Further inside the inner sheet, the innermost sheet is provided and this innermost sheet prevents the inner sheet from coming in contact with the wearer's skin. The innermost sheet is joined, in the regions extending in the vicinity of the ends thereof opposite in the front-back direction A, to at least one of the inner sheet and the outer sheet. The innermost sheet includes, in its region defined on the transverse center line P of the diaper, the tuck extending downward toward the inner sheet.

17 Claims, 4 Drawing Sheets

(56) References Cited

U.S. PATENT DOCUMENTS

| | | | |
|---|---|---|---|
| 4,430,086 A * | 2/1984 | Repke | 604/385.26 |
| 6,123,692 A * | 9/2000 | Guidotti et al. | 604/385.01 |
| 6,132,409 A * | 10/2000 | Vogt et al. | 604/348 |
| 6,152,908 A * | 11/2000 | Widlund et al. | 604/385.19 |
| 6,409,711 B1 * | 6/2002 | Jonbrink | 604/385.01 |
| 6,508,798 B1 | 1/2003 | Widlund et al. | |
| 2004/0039363 A1 | 2/2004 | Sugiyama et al. | |
| 2005/0143710 A1 * | 6/2005 | Van Gompel et al. | 604/393 |

FOREIGN PATENT DOCUMENTS

| | | |
|---|---|---|
| JP | 67725 | 2/1994 |
| JP | 9510385 | 10/1997 |
| JP | 2002011044 | 1/2002 |
| JP | 2002204811 | 7/2002 |
| JP | 2003126143 | 5/2003 |
| JP | 2003305080 | 10/2003 |
| JP | 2004000414 | 1/2004 |
| JP | 2007209522 | 8/2007 |
| WO | 9525494 | 9/1995 |

* cited by examiner

PANTS TYPE DISPOSABLE DIAPER

RELATED APPLICATIONS

The present application is based on, and claims priority from, International Application No. PCT/JP2008/072819 filed Dec. 16, 2008 Japanese Application Number 2008-006555, filed Jan. 16, 2008, the disclosure of which is hereby incorporated by reference herein in its entirety.

TECHNICAL FIELD

The present invention relates to a pants type disposable diaper and, more particularly, to such a diaper having a capability to prevent a top-sheet covering a liquid-absorbent core from coming in contact with a wearer's skin.

RELATED ART

It is conventionally well known to provide a disposable diaper on a side closer to a wearer's skin than a top-sheet constituting a bodily fluid-absorbent structure with an additional piece of sheet material adapted to be spaced from the top-sheet in the thickness direction of the bodily fluid-absorbent structure. It is also well known to form such an additional piece of sheet material with let-through openings for passage of feces and/or urine to be guided toward the bodily fluid-absorbent structure. Body waste such as feces and urine is retained within an open space serving as a pocket or pockets defined between the additional piece of sheet material and the top-sheet. The additional piece of sheet material serves to prevent the top-sheet soiled with the body waste such as feces from coming in contact with the wearer's skin.

For example, an open-type disposable diaper disclosed in Japanese Patent Application Laid-Open Publication No. 1993-305109 (PATENT DOCUMENT 1) includes a liquid-resistant second top-sheet lying on the side of a first top-sheet covering a liquid-absorbent core facing a wearer's skin and formed with an opening dimensioned to be relatively long in a front-back direction of the diaper. The opening has elastic members attached thereto under tension along both side edges thereof. Upon contraction of these elastic members, the second top-sheet is spaced upward from the first top-sheet and body waste discharged by the diaper wearer passes through the opening into an open space defined between these two top-sheets.

An open-type diaper disclosed in Japanese Patent Application, based on a Japanese translation of PCT international application Laid-Open Publication No. 1997-510385 (PATENT DOCUMENT 2) includes a pair of side flaps attached to the inner surface of a chassis along respective side edges thereof and joined together in a crotch region so as to form an open space adapted to retain feces between a liquid-pervious sheet covering an absorbent structure and these side flaps. Once feces has passed the opening defined between these side flaps and retained within the open space, feces is restricted to come in contact with the wearer's skin. The respective side flaps include elastic members attached thereto under tension along free edges thereof.

The pants type diaper disclosed in Japanese Patent Application Laid-Open Publication No. 2002-11044 (PATENT DOCUMENT 3) includes a skin-contact sheet above a liquid-pervious top-sheet covering an absorbent structure. A portion of the skin-contact sheet adapted to be spaced upward from the top-sheet is formed with an opening around which an elastic member is attached under tension to the skin-contact sheet. Feces discharged by a diaper wearer passes through the opening into an open space defined between the skin-contact sheet and the top-sheet and, in consequence, feces does not come in contact with the wearer's skin. The presence of the skin-contact sheet eliminates a possibility that the top-sheet wetted with bodily fluids might come in contact with the wearer's skin.

PATENT DOCUMENT 1: Japanese Patent Application Laid-Open Publication No. 1993-305109

PATENT DOCUMENT 2: Japanese Patent Application, based on a Japanese translation of PCT international application, Laid-Open Publication No. 1997-510385

PATENT DOCUMENT 3: Japanese Patent Application Laid-Open Publication No. 2002-11044

DISCLOSURE OF THE INVENTION

Problem to be Solved by the Invention

In every case of the above-described diapers of prior art, an additional piece of sheet material such as the second top-sheet arranged above the liquid-permeable first top-sheet covering the bodily fluid-absorbent core may have its dimension in the front-back direction apparently be reduced under contraction of the elastic members. Certainly such contraction allows the additional piece of sheet material to be spaced upward from the top-sheet and to form the open space between the additional piece of sheet material and the top-sheet adapted to retain feces therein. However, from a standpoint of convenience for putting the diaper on the wearer's body and feeling to wear, some problems are unsolved behind. Specifically, contraction of the elastic members may create many deep gathers which may complicate the inside geometry of the diaper and interrupt handling operation of a mother or a helper to guide the wearer's legs through the leg-openings of the diaper. If such gathers are formed in the crotch region having relatively a small width, it may be difficult for the wearer to feel a snug fitting.

In view of the problems as have been described above, it is a principal object of the present invention to provide a pants type disposable diaper improved in comparison with the diapers of prior art in the above.

Measure to Solve the Problem

The object set forth above is achieved, according to the present invention, by an improvement in a pants type disposable diaper having a front-back direction, a transverse direction and a longitudinal direction which are orthogonal one to another and a crotch region, a front waist region extending forward from the crotch region and a rear waist region extending rearward from the crotch region which cooperate together to define a waist-opening and a pair of leg-openings, the pants type disposable diaper further including a bodily fluid-absorbent structure lying in the crotch region and formed by a bodily fluid-absorbent core sandwiched between a liquid-permeable inner sheet and a liquid-impermeable outer sheet and an innermost sheet and the innermost sheet lying further inside the inner sheet and having a region adapted to be spaced upward from the inner sheet in thickness direction of the core and functioning as a separator to prevent the inner sheet from coming in direct contact with a wearer's skin.

The improvement according to the present invention is characterized in that the innermost sheet is joined to at least one of the inner sheet and the outer sheet in end regions thereof opposed to each other in the front-back direction and lying on a front-back center line extending in the front-back direction so as to bisect a dimension of the diaper in the transverse direction and adapted, in a region thereof defined between the end regions, to be spaced upward from the inner sheet in the thickness direction of the core; and the innermost sheet is formed on a transverse center line extending in the transverse direction so as to bisect a dimension of the diaper in said front-back direction with a tuck extending downward from the region adapted to be spaced upward from the inner sheet toward the inner sheet.

According to one preferred embodiment of the present invention, the innermost sheet has at least one of a front let-through opening formed in front of the transverse center line so as to allow urine discharged by the wearer to flow not through the innermost sheet but directly to the bodily fluid-absorbent structure and a rear let-through opening formed in the rear of the transverse center line so as to allow feces discharged by the wearer to move not through the innermost sheet but directly to the bodily fluid-absorbent structure.

According to another preferred embodiment of the present invention, the tuck is formed by partially joining regions of the innermost sheet put flat together as the diaper is folded along the transverse center line.

According to still another preferred embodiment of the present invention, the innermost sheet is a piece of sheet material having an hourglass-like planar shape and folded along the transverse center line which is elastically stretchable and contractible in the transverse direction in the front and rear waist regions but neither stretchable nor contractible elastically as well as non-elastically at least in a section defined along the transverse center line in the crotch region.

According to yet another preferred embodiment of the present invention, the bodily fluid-absorbent structure is provided in a form of a panel and any one of the inner sheet and the outer sheet extending outward beyond the peripheral edge of the core is joined to the outer surface of the innermost sheet.

EFFECT OF THE INVENTION

The pants type disposable diaper according to the present invention is provided further inside the liquid-permeable inner sheet with the innermost sheet. The innermost sheet includes the region extending in the front-back direction along the front-back centerline and adapted to be spaced upward from the inner sheet and functioning as a separator to prevent the inner sheet from coming in contact with the wearer's skin. The region functioning as the separator is formed with the tuck extending downward from the innermost sheet toward the inner sheet and has its dimension in the front-back direction which is reduced by a dimension to form the tuck. In consequence, the region does not have noticeable gathers or sag.

The other effects provided by the preferred embodiments of the present invention will be described later in details.

IDENTIFICATION OF REFERENCE NUMERALS USED IN THE DRAWINGS

Figure 1:
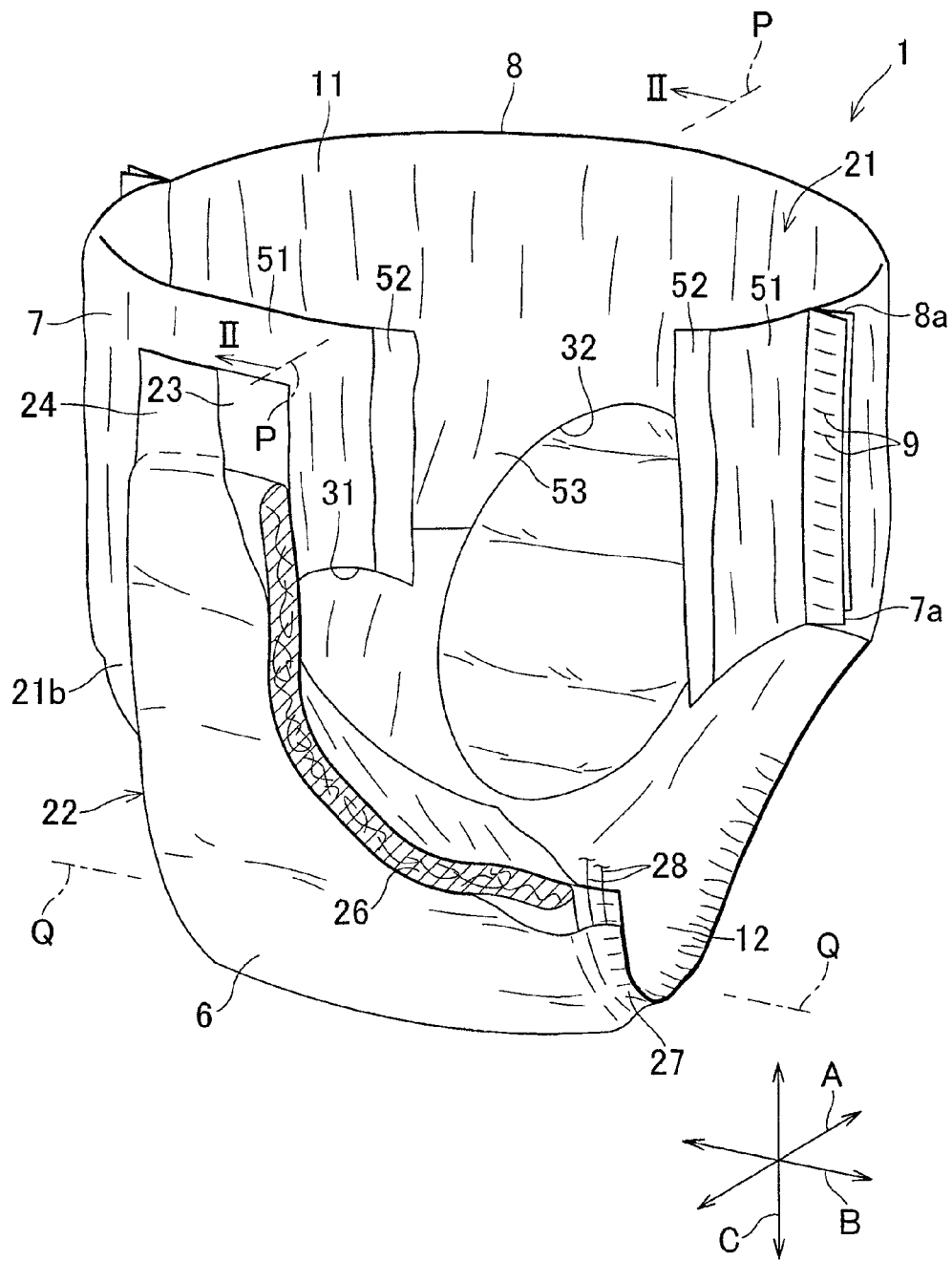
FIG. 1 is a partially cutaway perspective view of a pants type disposable diaper.

1 pants type disposable diaper
6 crotch region
7 front waist region
8 rear waist region
11 waist-opening
12 leg-openings
21 innermost sheet
23 inner sheet
24 outer sheet
26 core
31 front let-through opening
32 rear let-through opening
36 tuck
A front-back direction
B transverse direction
C longitudinal direction
P front-back center line
Q transverse center line
R longitudinal center line

DETAILED DESCRIPTION OF THE PREFERRED EMBODIMENTS

Details of a pants type disposable diaper according to the present invention will be more fully understood from the following description given in reference to the accompanying drawings.

FIG. 1 is a partially cutaway perspective view of a pants type disposable diaper 1 put on a wearer's body wherein a front-back direction, a transverse direction and a longitudinal direction are indicated by double-headed arrows A, B and C being orthogonal one to another. The diaper 1 comprises a crotch region 6, a front waist region extending forward from the crotch region 6 and a rear waist region 8 extending rearward from the crotch region 6 wherein side edges 7a, 7a of the front waist region 7 are put flat and fusion-bonded together with side edges 8a, 8a of the rear waist region 8 at seam spots 9 arranged intermittently in the longitudinal direction C. The diaper 1 further includes a waist-opening 11, a pair of leg-openings 12, an innermost sheet 21 directly facing the wearer's skin (not shown) and a bodily fluid-absorbent structure 22 attached to the outer surface 21b of the innermost sheet 21. Sections of the innermost sheet 12 defining the front and rear waist regions 7, 8 are elasticized to be stretchable and contractible in the transverse direction B while the section of the innermost sheet 12 defining the crotch region 6 is set substantially over its entire area to be non-stretchable elastically as well as non-elastically. While the innermost sheet 21 is preferably liquid-impermeable over its entire area and more preferably air-permeable but liquid-impermeable in its entire area, it is possible to make up the innermost sheet in a manner that the section defining the front and rear waist regions 7, 8 is liquid-impermeable and the section defining the crotch region 6 is liquid-permeable. The bodily fluid-absorbent structure comprises a liquid-permeable inner sheet 23, a liquid-impermeable outer sheet 24 and a core 26 formed by bodily fluid-absorbent material wrapped with a piece of tissue paper and sandwiched between the sheets 23, 24 wherein these two sheets 23, 24 extend outward beyond the peripheral edge of the core 26 and put flat and joined together. At least one of these two sheets 23, 24 is joined to the innermost sheet 21. Along both side edges 27 of the crotch region 6, the innermost sheet 21, the inner sheet 23 and the outer sheet 24 are put flat and joined together. Also along these side edges 27, leg-surrounding elastic members 28 extending are sandwiched between the inner sheet 23 and the outer sheet 24 and bonded under tension to at least one of these two sheets 23, 24. Between the side edges 27, the innermost sheet 21 and the inner sheet 23 are spaced from each other in the thickness direction of the core 26. The innermost sheet 21 is formed ahead of the transverse center line Q-Q extending in the transverse direction B and bisecting a dimension of the diaper 1 in the front-back direction A with a front let-through opening 31 and in the rear of the transverse center line Q-Q with a rear let-through opening 32. The front let-through opening 31 is located so that the wearer's external genital may be exposed within this opening and the rear let-through opening 32 is located so that the wearer's anus may be exposed within this opening. With such a manner of the locations, urine and/or feces discharged by the diaper wearer can flow directly to the bodily fluid-absorbent structure 23 without permeating the innermost sheet 21. Urine having passed through the front let-through opening 31 as well as feces having passed through the rear let-through opening 32 can be securely retained within an open space defined between the innermost sheet 21 and the inner sheet 23 and, in consequence, such urine and/or feces will not come in contact with the diaper wearer's skin.

Figure 2:
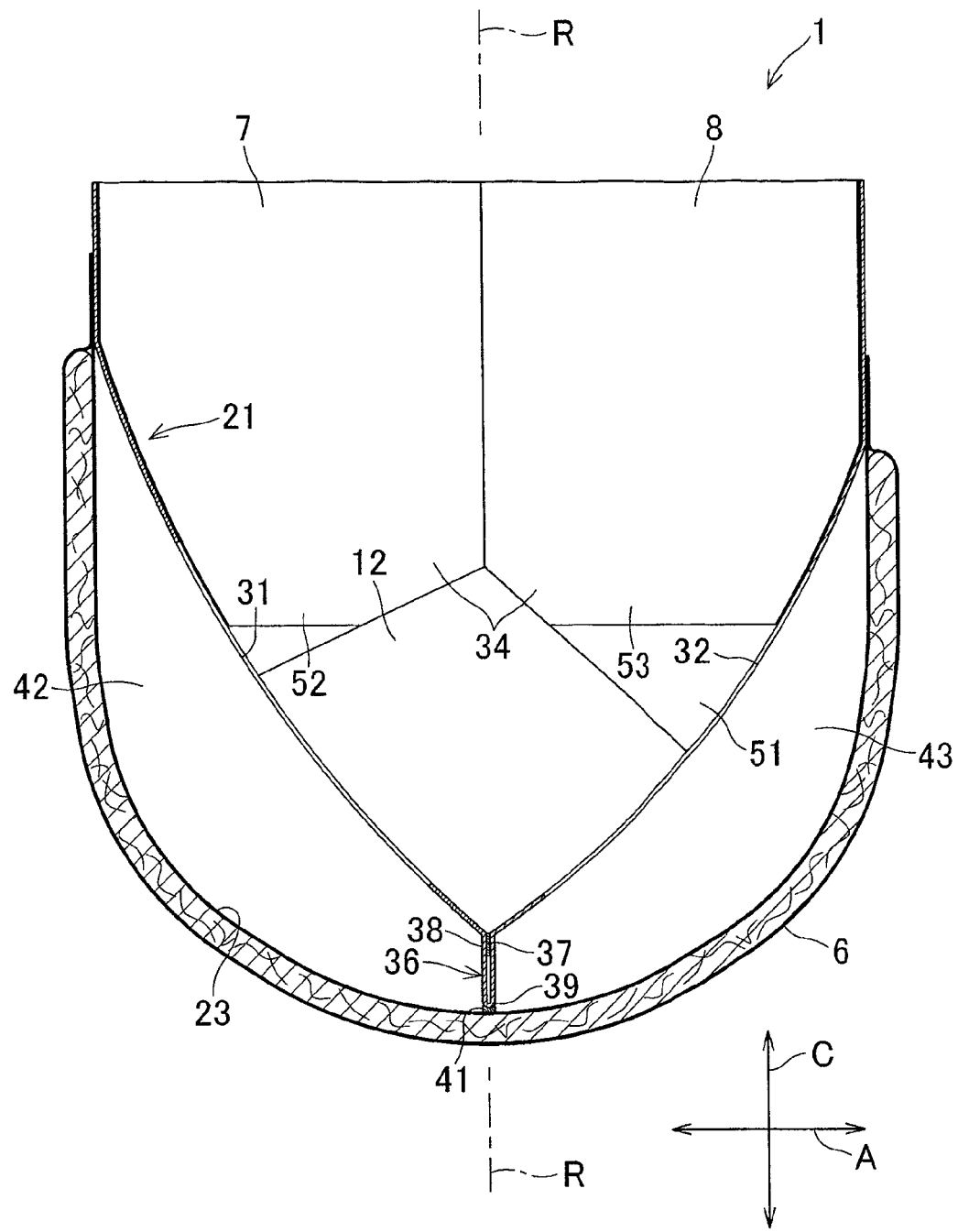
FIG. 2 is a sectional view taken along a line II-II in FIG. 1.

FIG. 2 is a sectional view taken along a line II-II in FIG. 1 corresponding to the front-back center line P extending in the front-back direction A so as to bisect the dimension of the diaper 1 in the transverse direction B. The sections of the innermost sheet 21 lying in the front and rear waist regions 7, 8 are joined to each other in parallel to the longitudinal center line R extending in the longitudinal direction C so as to bisect a dimension of the diaper 1 in the front-back direction A and to form upper edges of the respective leg-openings 12. In the crotch region 6, the innermost sheet 21 is formed with a tuck 36. The tuck 36 is formed by adhesive-bonding or fusion-bonding the innermost sheet 21 to itself in a joint region 37 set on the longitudinal center line R so that, between the front let-through opening 31 and the rear let-through opening 32, the innermost sheet 21 is folded on itself along the longitudinal center line R. In other words, the tuck 36 extends downward from the section of the innermost sheet 21 spaced upward from the inner sheet 23 toward the inner sheet 23 along the longitudinal center line R (See FIG. 1). While the joint region 37 for the tuck 36 is illustrated to be defined in the vicinity of the top 38 of the tuck 36, a dimension of the joint region 37 may be appropriately enlarged toward the bottom 39 of the tuck 36. While a dimension of the joint region 37 in the transverse direction B is illustrated to be smaller than the width dimension of the crotch region 6, the dimension of the joint region 37 may be enlarged unless the joint region 37 interferes with smooth handling of a mother or a helper to put the diaper 1 on the wearer's body. For example, in a case of the diaper 1 for baby use, the dimension of this joint region 37 is preferably in a range of 5 to 30 mm. It is also possible to join the bottom 39 of the tuck 36 to the inner sheet 23 by appropriate joining means such as adhesive applied to the outer surface of the bottom 39. It should be noted that not only the section of the innermost sheet 21 forming the bottom 39 of the tuck 36 but also entire sections thereof lying transversely on both sides of the bottom 39 may be bonded to the inner sheet 23 (See FIG. 4).

Between the innermost sheet 21 and the inner sheet 23, a front open space 42 is formed ahead of the transverse center line Q and a rear open space 43 is formed in the rear of the transverse center line Q. The tuck 36 is formed between these two open spaces 42, 43. The front let-through opening 31 of the innermost sheet 21 ensures communication of the front open space 42 with its outside, allowing urine to flow into the front open space 42. Similarly, the rear let-through opening 32 ensures communication of the rear open space 43 with its outside, allowing feces to move into the rear open space 43.

Figure 3:
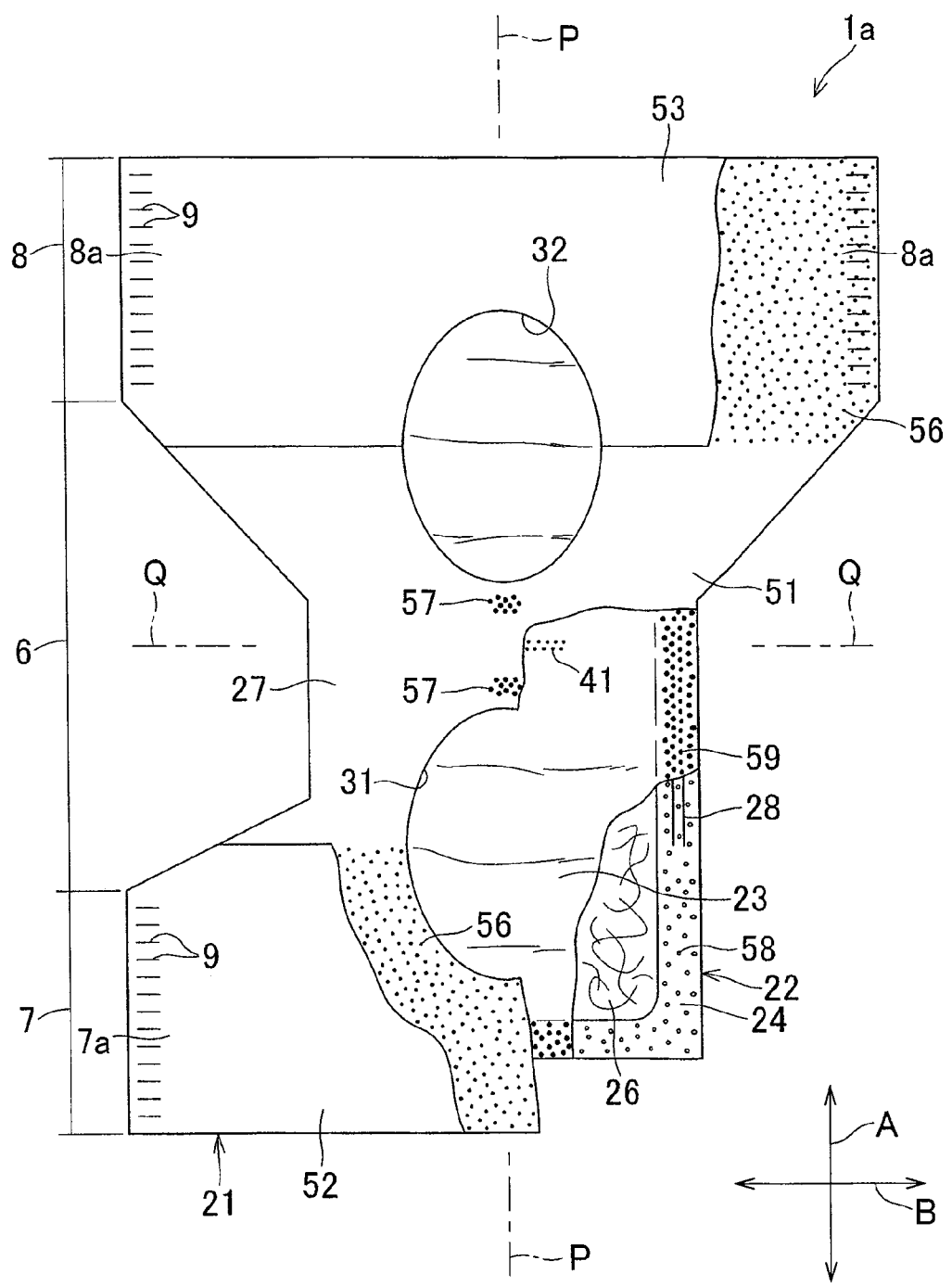
FIG. 3 is a partially cutaway plan view showing the diaper in a flatly developed state.

FIG. 3 is a partially cutaway plan view of the flatly developed diaper 1a obtained from the diaper 1 of FIGS. 1 and 2 by disjoining the front and rear waist regions 7, 8 from each other at the seams 9, breaking the joint region 37 of the tuck 36 along which the innermost sheet 21 has been joined to itself and developing the crotch region 6 and the front and rear waist regions 7, 8 in the front-back direction A as well as in the transverse direction B against contractile force of the elastic members. For convenience, the regions of the diaper 1a common to those of the diaper 1 are designated by reference numerals same as those in the diaper 1.

In the flatly developed diaper 1a, the innermost sheet 21 is formed by a composite sheet consisting of a first sheet 51, a second sheet 52 and a third sheet 53. The first sheet 51 is substantially hourglass-shaped and comprises the crotch region 6 and the front and rear waist regions 7, 8. The first sheet 51 is neither stretchable nor contractible elastically as well as non-elastically and faces the inner sheet 23. The second sheet 52 is elastically stretchable and contractible in the transverse direction B and attached under tension to the inner surface of the first sheet 51 by means of hot melt adhesive 56 in the front waist region 7 and a part of the crotch region 6. The third sheet 53 is elastically stretchable and contractible in the transverse direction B and attached under tension to the inner surface of the first sheet 51 by means of hot melt adhesive 56 in the rear waist region 8 and a part of the crotch region 6. A pair of regions 57 provided on the inner surface of the first sheet 51 each indicated by a plurality of dots in FIG. 3 correspond to the joint region 37 in FIG. 2 and are symmetrically located about the transverse center line Q.

In the bodily fluid-absorbent structure 22, the inner sheet 23 and the outer sheet 24 sandwiching the core 26 therebetween extend outward beyond the peripheral edge of the core 26 and put flat and bonded together by means of hot melt adhesive 58 outside the peripheral edges of the core 26. Along both side edges 27 of the crotch region 6 in the flatly developed diaper 1a include leg-surrounding elastic members 28 sandwiched between the inner sheet 23 and the outer sheet 24 and extending under tension in the front-back direction A. The peripheral edge of the inner sheet 23 is bonded to the outer surface of the innermost sheet 21 by means of hot melt adhesive 59. The outer sheet 24 is preferably dimensioned to be same as the inner sheet 23 in shape as well as in size or to be slightly larger than the inner sheet 23. The outer sheet 24 dimensioned to be slightly larger than the inner sheet 23 preferably has its peripheral edge extending outward beyond the peripheral edge of the inner sheet 23 bonded to the outer surface of the innermost sheet 21.

According to the illustrated embodiment, the innermost sheet 21 has sections defined in the vicinity of its opposite ends but lying on extensions of the crotch region 6 bonded to the bodily fluid-absorbent structure 22 by means of adhesive 59 and an intermediate section between these two regions bonded to the bodily fluid-absorbent structure 22 by means of hot melt adhesive 41.

To obtain the diaper 1 from the flatly developed diaper 1a, the flatly developed diaper 1a may be folded along the transverse center line Q on itself with the innermost sheet 21 inside, joining the regions 57 of the first sheet 51 to each other and joining the side edges 7a, 7a of the front waist region 7 to the side edges 8a, 8a of the rear waist region 8 at the seam spots 9 (See FIG. 1).

With this diaper 1 put on the wearer's body, the innermost sheet 21 in the crotch region 6 is spaced upward from the inner sheet 23 covering the bodily fluid-absorbent structure 22 and thereby functions as a separator which is capable of preventing the inner sheet 23 soiled with feces and/or urine from coming in contact with the wearer's skin. Of the innermost sheet 21, the section defining the tuck 36 cooperates with the sections respectively extending outward from the tuck 36 in the transverse direction B to define a partitioning wall for the front open space 42 and the rear open space 43, which is capable of preventing urine and feces from being mixed together. In this way, the diaper 1 is free from a trouble that feces might be mixed with urine and changed to low viscous ones which are easy to soil the wearer's skin in a broad area. Furthermore, the length dimension of the innermost sheet 21 in the front-back direction A along the front-back center line P in FIG. 3 is reduced in the diaper 1 of FIGS. 1 and 2 not by a contraction of elastic members but by the formation of the tuck 36. Consequentially, with the diaper 1 put on the wearer's body, the innermost sheet 21 in the crotch region 6 might not be formed with many wrinkles. In other words, when a mother or a helper looks down the interior of the diaper 1 before putting the diaper 1 on the wearer's body, the leg-openings 12 might not be hidden by the wrinkled innermost sheet 21. Thus the mother or the helper can smoothly guide the wearer's legs into the leg-openings 12. In the case of the diaper 1 having been put on the wearer's body in this manner the crotch region 6 might not become bulky due to the wrinkles and the diaper 1 will snugly fit the wearer's body.

In the front and rear waist regions 7, 8 of the exemplarily illustrated diaper 1, the elasticized second and third sheets 52, 53 are attached to the inner surface of the non-elasticized first sheet 51, respectively, so that the first sheet 51 defining the outer surface of the diaper 1 in the state as illustrated by FIGS. 1 and 2 may be formed with many gathers on the outer side but the second and third sheets 52, 53 defining the inner surfaces of the front and rear waist regions 7, 8 may remain smooth. In consequence, the wearer's skin might not be irritated by gathers which would otherwise be formed on the inner surfaces of the front and rear waist regions 7, 8. However, if such an effect provided by the second and third sheets 52, 53 is not required, the second and third sheets 52, 53 may be attached under tension to the outer surface of the first sheet 51.

While the innermost sheet 21 of the diaper 1 is preferably liquid-impermeable and more preferably air-permeable and liquid-impermeable, it is possible to form the innermost sheet 21 by a composite sheet comprising two component sheets having properties different from each other so that the innermost sheet 21 may be liquid-permeable in the crotch region 6 but liquid-impermeable in the front and rear waist regions 7, 8. For example, a piece of non-woven fabric formed by thermoplastic synthetic fiber or a piece of film formed by thermoplastic synthetic resin may be used as the first sheet 51 in the innermost sheet 21. It is also possible to use a laminated sheet consisting of two or more non-woven fabric layers or a laminated sheet consisting of a non-woven fabric layer and a plastic film layer. As stock materials for the second and third sheets 52, 53, elastically stretchable and contractible non-woven fabric containing elastic filaments such as urethane filaments or elastically stretchable and contractible film made of, for example, natural or synthetic rubber may be used. As stock materials for the inner sheet 23, although not meant to be limiting, liquid-permeable non-woven fabric, thermoplastic film or composite sheet consisting of a non-woven fabric layer and a plastic film layer laminated on each other may be used. As stock materials for the outer sheet, although not meant to be limiting, liquid-impermeable non-woven fabric, thermoplastic film or composite sheet consisting of a non-woven fabric layer and a plastic film layer laminated on each other may be used.

Figure 4:
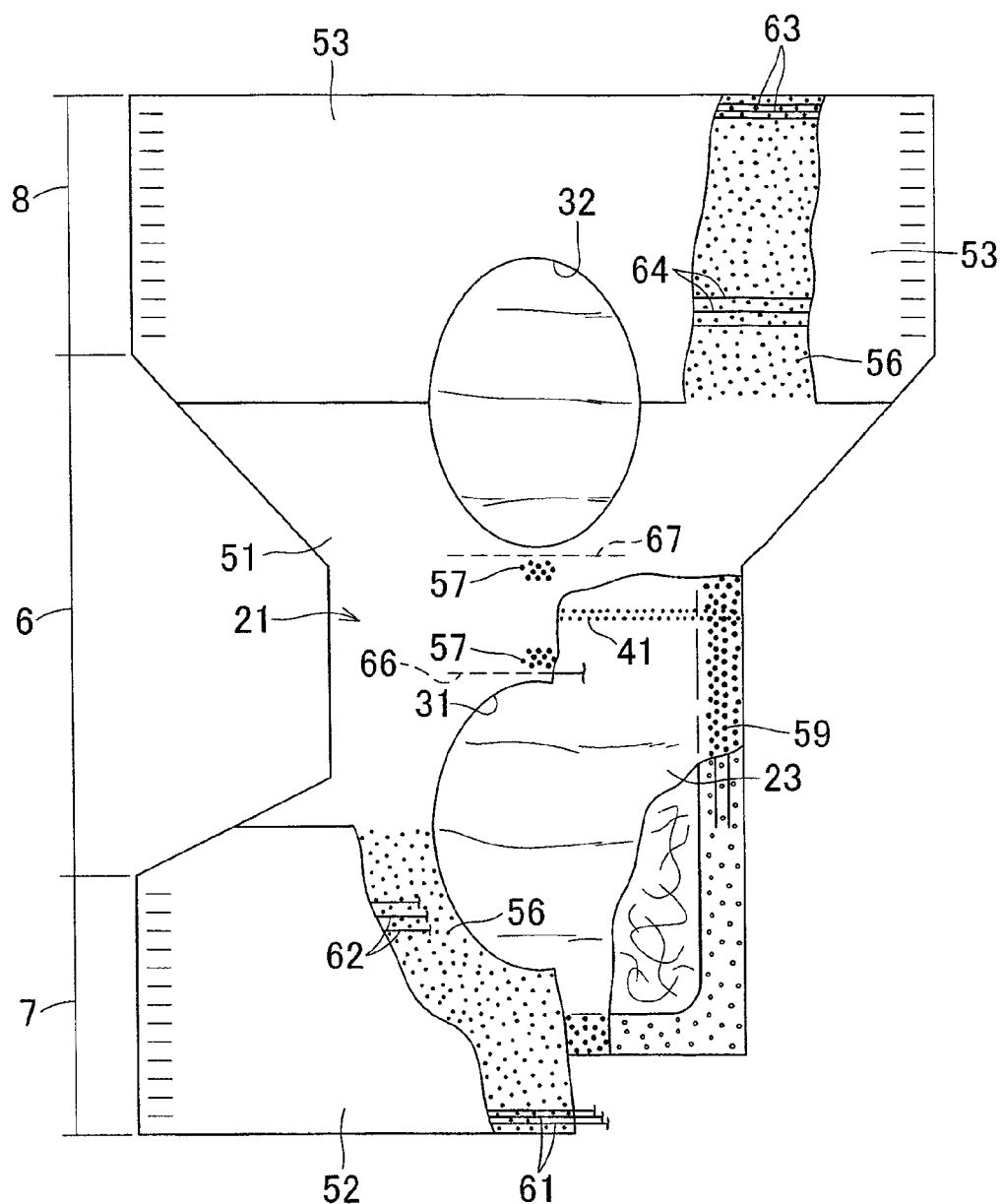
FIG. 4 is a view similar to FIG. 3, showing one embodiment of the pants type disposable diaper in a flatly developed state.

FIG. 4 is a view similar to FIG. 3, illustrating another embodiment of the present invention. In the flatly developed diaper 1a depicted in FIG. 4, the innermost sheet 21 comprises the first sheet 51 which is substantially hourglass-shaped and not stretchable elastically as well as non-elastically, the second sheet 52 which is also not stretchable elastically as well as non-elastically and attached to the inner or outer surface of the front waist region 7 plus a part of the crotch region 6 of the first sheet 51 by means of hot melt adhesive 56 and the third sheet 53 attached to the inner or outer surface of the rear waist region 8 plus a part of the crotch region 6 of the first sheet 51 by means of hot melt adhesive 56. To any one of the first sheet 51 and the second sheet 52, two or more first elastic members 61 extending in the transverse direction B are attached under tension in the vicinity of the waist-opening 11 and two or more second elastic members 62 extending in the transverse direction B are attached under tension in the vicinity of the crotch region 6. To any one of the first sheet 51 and the third sheet 53, two or more third elastic members 63 extending in the transverse direction B are attached under tension in the vicinity of the waist-opening 11 and two or more fourth elastic members 64 are attached under tension in the vicinity of the crotch region 6. To the outer surface of the first sheet 51 in the crotch region 6, crotch region elasticizing members 66, 67 extending in the transverse direction B between the region 57 and the front let-through opening 31 and between the region 57 and the rear let-through opening 32, respectively, are attached under tension. The outer surface of the first sheet 51 is attached, in its section extending fully across the crotch region 6 along the transverse center line Q, to the inner sheet 23 by means of hot melt adhesive 41.

With the diaper 1 obtained from the flatly developed diaper 1a depicted in FIG. 4, the first through fourth elastic members 61 through 64 allow the front and rear waist regions 7, 8 of the diaper 1 to put in contact around the wearer's waist snugly. While the crotch region elasticizing members 66, 67 are not essential for the diaper 1, these members 66, 67 facilitates the section of the innermost sheet 21 extending in the vicinity of the tuck 36 to fit snugly around the thighs and the other areas of the wearer.

While the innermost sheet 21 is preferably formed with the front let-through opening 31 and the rear let-through opening 32 for the diaper 1, the innermost sheet 21 may be formed with only one let-through opening without departing from the scope of the present invention.

The invention claimed is:

1. A pants type disposable diaper having a front-back direction, a transverse direction and an up-down direction which are orthogonal one to another, said disposable diaper comprising:
   a crotch region;
   a front waist region extending forward from said crotch region in the front-back direction;
   a rear waist region extending rearward from said crotch region in the front-back direction, wherein said front waist region, said rear waist region and the crotch region together define a waist-opening and a pair of leg-openings,
   a bodily fluid-absorbent structure lying in said crotch region and including
      a liquid-permeable inner sheet;
      a liquid-impermeable outer sheet;
      a bodily fluid-absorbent core sandwiched between the liquid-permeable inner sheet and the liquid-impermeable outer sheet; and
   an innermost sheet lying on a skin-facing side of said inner sheet and having a region adapted to be spaced upward from said inner sheet in a thickness direction of said core to prevent said inner sheet from coming into direct contact with a wearer's skin in use, wherein
said innermost sheet is joined to at least one of said inner sheet and said outer sheet in end regions thereof opposed to each other in said front-back direction and lying on a front-back center line extending in said front-back direction so as to bisect a dimension of said diaper in said transverse direction,
said innermost sheet is folded inwardly to face itself along a transverse center line extending in said transverse direction so as to bisect a dimension of said diaper in said front-back direction to form a tuck extending downward toward said inner sheet from said region adapted to be spaced upward from said inner sheet, and
said innermost sheet is elastically stretchable and contractible in the transverse direction in said front and rear waist regions, but neither stretchable nor contractible elastically as well as non-elastically at least in a section defined along the transverse center line in said crotch region.

2. The diaper defined by claim 1, wherein said innermost sheet further has at least one of
a front through opening formed in front of said transverse center line so as to allow urine discharged by the wearer of said diaper to flow directly to said bodily fluid-absorbent structure and
a rear through opening formed in rear of said transverse center line so as to allow feces discharged by said wearer to pass directly to said bodily fluid-absorbent structure.

3. The diaper defined by claim 2, further comprising crotch region elasticizing members attached to an outer surface of the innermost sheet and extending in the transverse direction, and said outer surface faces toward the bodily fluid-absorbent core.

4. The diaper defined by claim 3, wherein
said innermost sheet has joining regions which are joined together to define said tuck in which the joining regions of said innermost sheet are put flat and bonded together as said innermost sheet is folded along said transverse center line, and
said crotch region elasticizing members are arranged in the crotch region, between one of the joining regions and the front through opening, and between another joining region and the rear through opening, respectively.

5. The diaper defined by claim 1, wherein said innermost sheet has joining regions which are joined together to define said tuck in which the joining regions of said innermost sheet are put flat and bonded together as said innermost sheet is folded along said transverse center line. inner sheet and said outer sheet extending outward beyond a peripheral edge of said core is joined to the outer surface of said innermost sheet.

6. The diaper defined by claim 5, wherein
said tuck comprises a top portion and a bottom portion in the up-down direction, and an intermediate portion between the top portion and the bottom portion in the up-down direction.

7. The diaper defined by claim 6, wherein the joining regions are joined together at the top portion of the tuck, and the innermost sheet is bonded to the inner sheet at the bottom portion of the tuck.

8. The diaper defined by claim 7, wherein the joining regions of the innermost sheet are free of direct bonding to each other in the intermediate portion of the tuck.

9. The diaper defined by claim 1, wherein said innermost sheet is a piece of sheet material having an hourglass planar shape.

10. The diaper defined by claim 1, wherein said bodily fluid-absorbent structure is in a form of a panel, and one of said inner sheet and said outer sheet extending outward beyond a peripheral edge of said core is joined to an outer surface of said innermost sheet, said outer surface facing toward the bodily fluid-absorbent core.

11. The diaper defined be claim 1, wherein the innermost sheet is liquid-permeable in the crotch region, and is liquid-impermeable in the front and rear waist regions.

12. The diaper defined by claim 1, wherein the innermost sheet comprises
a first sheet in the crotch region and the front and rear waist regions,
a second sheet in the front waist region, and
a third sheet in the rear waist region.

13. The diaper defined by claim 12, wherein
the first sheet is liquid-permeable, and
the second and third sheets are liquid-impermeable and directly attached to the first sheet at the front waist region and the rear waist region, respectively.

14. The diaper defined by claim 12, further comprising at least one of
a front through opening formed in front of said transverse center line so as to allow urine discharged by the wearer of said diaper to flow directly to said bodily fluid-absorbent structure and
a rear through opening formed in the rear of said transverse center line so as to allow feces discharged by said wearer to pass directly to said bodily fluid-absorbent structure.

15. The diaper defined by claim 14, wherein said front through opening is in the first sheet and partially in the second sheet, and said rear through opening is in the first sheet and partially in the third sheet.

16. A pants type disposable diaper having a front-back direction, a transverse direction and an up-down direction which are orthogonal one to another, said disposable diaper comprising:
a crotch region;
a front waist region extending forward from said crotch region in the front-back direction;
a rear waist region extending rearward from said crotch region in the front-back direction;
a bodily fluid-absorbent structure lying in said crotch region and including
a liquid-permeable inner sheet;
a liquid-impermeable outer sheet;
a bodily fluid-absorbent core sandwiched between the liquid-permeable inner sheet and the liquid-impermeable outer sheet; and
an innermost sheet lying on a skin-facing side of said inner sheet and having a region adapted to be spaced upward from said inner sheet in a thickness direction of said core and to prevent said inner sheet from coming into direct contact with a diaper wearer's skin in use,
wherein
said innermost sheet is joined to at least one of said inner sheet and said outer sheet in end regions thereof opposed to each other in said front-back direction,
said innermost sheet includes
an inner surface facing away from the bodily fluid-absorbent core, and
joining regions directly joined to each other at the inner surface upon folding said innermost sheet to define a tuck extending downward toward said inner sheet from said region adapted to be spaced upward from said inner sheet,
said innermost sheet is elastically stretchable and contractible in the transverse direction in said front and rear waist regions, but neither stretchable nor contractible elastically as well as non-elastically at least in a section defined along the transverse center line in said crotch region.

17. The diaper defined by claim 16, wherein said tuck comprises a top portion and a bottom portion in the up-down direction, and an intermediate portion between the top portion and the bottom portion in the up-down direction, and the inner surface is bonded to itself at the top portion and free of bonding to itself at the intermediate portion and the bottom portion.

\* \* \* \* \*